United States Patent
Decottignies et al.

(10) Patent No.: US 11,208,597 B2
(45) Date of Patent: Dec. 28, 2021

(54) COBALT CATALYST COMPRISING A SUPPORT CONTAINING A MIXED OXIDE PHASE INCLUDING COBALT AND/OR NICKEL PRODUCED USING A HYDROCARBON COMPOUND

(71) Applicant: IFP Energies nouvelles, Rueil-Malmaison (FR)

(72) Inventors: Dominique Decottignies, Saint-Genis-Laval (FR); Romain Chenevier, Peaugres (FR); Antoine Fecant, Brignais (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 9 days.

(21) Appl. No.: 16/342,810

(22) PCT Filed: Sep. 6, 2017

(86) PCT No.: PCT/EP2017/072289
§ 371 (c)(1),
(2) Date: Apr. 17, 2019

(87) PCT Pub. No.: WO2018/072921
PCT Pub. Date: Apr. 26, 2018

(65) Prior Publication Data
US 2020/0047161 A1 Feb. 13, 2020

(30) Foreign Application Priority Data
Oct. 17, 2016 (FR) ...................................... 1660044

(51) Int. Cl.
| | | |
|---|---|---|
| *B01J 23/40* | (2006.01) |
| *B01J 23/42* | (2006.01) |
| *C10G 2/00* | (2006.01) |
| *B01J 21/12* | (2006.01) |
| *B01J 23/75* | (2006.01) |
| *B01J 37/02* | (2006.01) |
| *B01J 37/08* | (2006.01) |
| *B01J 21/08* | (2006.01) |
| *B01J 23/00* | (2006.01) |

(52) U.S. Cl.
CPC .............. *C10G 2/332* (2013.01); *B01J 21/12* (2013.01); *B01J 23/75* (2013.01); *B01J 37/0203* (2013.01); *B01J 37/0205* (2013.01); *B01J 37/0236* (2013.01); *B01J 37/08* (2013.01); *B01J 21/08* (2013.01); *B01J 23/005* (2013.01)

(58) Field of Classification Search
CPC .... B01J 37/0203; B01J 37/0236; B01J 37/08; C10G 2/332
USPC ........................................................ 502/326
See application file for complete search history.

(56) References Cited

U.S. PATENT DOCUMENTS

| | | | |
|---|---|---|---|
| 8,618,182 B2 | 12/2013 | Diehl et al. | |
| 9,486,789 B2 | 11/2016 | Decottignies et al. | |
| 2010/0029792 A1* | 2/2010 | Diehl ....................... | B01J 21/12 518/715 |
| 2012/0149559 A1 | 6/2012 | Wolan et al. | |
| 2015/0266006 A1* | 9/2015 | Decottignies ............ | B01J 21/12 518/715 |

FOREIGN PATENT DOCUMENTS

| | | |
|---|---|---|
| FR | 2963345 B1 | 7/2012 |
| FR | 3018702 B1 | 10/2017 |
| WO | 12013866 A1 | 2/2012 |

OTHER PUBLICATIONS

International Search Report WO2017EP72289 dated Oct. 27, 2017 (pp. 1-4).

* cited by examiner

*Primary Examiner* — Haytham Soliman
(74) *Attorney, Agent, or Firm* — Millen, White, Zelano and Branigan, P.C.; Harry B. Shubin

(57) ABSTRACT

The invention relates to a catalyst containing an active cobalt phase, deposited on a support comprising alumina, silica or silica-alumina, said support also containing a mixed oxide phase containing cobalt and/or nickel, said catalyst having been prepared by introducing at least one hydrocarbon organic compound of formula $C_xH_y$. The invention also relates to the use thereof in the field of Fischer-Tropsch synthesis processes.

13 Claims, No Drawings

COBALT CATALYST COMPRISING A SUPPORT CONTAINING A MIXED OXIDE PHASE INCLUDING COBALT AND/OR NICKEL PRODUCED USING A HYDROCARBON COMPOUND

The invention relates to a catalyst containing an active cobalt phase, deposited on a support comprising alumina, silica or silica-alumina, said support also containing a mixed oxide phase containing cobalt and/or nickel, said catalyst having been prepared by introducing at least one hydrocarbon organic compound of formula $C_xH_y$. The invention also relates to the method for preparing same and to the use thereof in the field of Fischer-Tropsch synthesis processes.

The present invention relates to the field of Fischer-Tropsch synthesis processes that make it possible to obtain a wide range of hydrocarbon cuts from the $CO+H_2$ mixture, commonly referred to as synthesis gas or syngas.

The simplified stoichiometric equation (limited in the equation below to the formation of alkanes) of the Fischer-Tropsch synthesis is written:

$$nCO+(2n+1)H_2 \rightarrow C_nH_{2n+2}+nH_2O$$

The catalysts used in Fischer-Tropsch synthesis are usually supported catalysts based on alumina, silica or silica-alumina or combinations of these supports, the active phase mainly consisting of iron (Fe) or cobalt (Co) optionally doped with a noble metal such as Pt, Rh or Ru.

The addition of an organic compound to Fischer-Tropsch catalysts to improve their activity was recommended by a person skilled in the art.

Many documents describe the use of various ranges of organic compounds as additives, such as nitrogen-containing organic compounds and/or oxygen-containing organic compounds.

In particular, U.S. Pat. Nos. 5,856,260 and 5,856,261 respectively teach the introduction, during the preparation of the catalyst, of polyols of general formula $CnH_{2n+2}O_x$ with n being an integer between 2 and around 6, and x being an integer between 2 and 11 or sugars of monosaccharide or disaccharide type, sucrose being particularly preferred.

Patent application US 2005/0026776 teaches the use of chelating compounds of the following types: nitrilotriacetic acid (NTA), trans-1,2-diaminocyclohexane-N,N,N',N'-tetraacetic acid (CyDTA) or ethylenediaminetetraacetic acid (EDTA), or else glycine, aspartic acid or citric acid for obtaining a catalyst with a reduced size of $Co_3O_4$ crystallites. Other documents teach the use of polyethers (WO 2014/092278 and WO 2015/183061), glyoxylic acid (WO 2015/183059), unsaturated dicarboxylic acids (US 2011/0028575) or else of multifunctional carboxylic acids of formula HOOC—$(CRR^1)_n$—COOH with $n \geq 1$ in the preparation of Fischer-Tropsch catalysts (WO 98/47618). Patent application US 2014/0353213 describes the use of lactams or cyclic esters of lactone type containing one oxygen atom in the ring (β-propiolactone, γ-butyrolactone, δ-valerolactone) or several oxygen atoms in the ring (propylene carbonate) in order to increase the activity of a catalyst of CoMo and NiMo type used in hydrodesulfurization of a diesel cut.

Document WO 2012/013866 discloses the use of a cyclic oligosaccharide, in particular cyclodextrin, as additive of a Fischer-Tropsch catalyst. This document also describes the use of a support based on silica-alumina optionally containing a spinel.

Document US 2010/236988 describes catalysts comprising a support loaded with an active metal that is brought into contact with a solution containing a hydrocarbon oil and a polar additive having a dipole moment of at least 0.45.

However, none of the documents relating to the additives describes a catalyst based on cobalt deposited on a support containing a mixed oxide phase containing cobalt and/or nickel prepared by means of a hydrocarbon organic compound of formula $C_xH_y$.

Irrespective of the compounds selected, the induced modifications do not always make it possible to increase the catalyst performance enough to make the process profitable. Furthermore, it is often very complicated to carry out the industrial deployment thereof as the methods are complex to implement.

Consequently, it appears essential, for catalyst manufacturers, to find new catalysts for Fischer-Tropsch synthesis with improved performance.

SUMMARY

One subject of the invention is a catalyst containing an active cobalt phase, deposited on a support comprising alumina, silica or silica-alumina, said support further containing a mixed oxide phase containing cobalt and/or nickel, said catalyst being prepared by a process comprising at least:
 a) a step of bringing a support comprising alumina, silica or silica-alumina into contact with at least one solution containing at least one precursor of cobalt and/or of nickel, then drying and calcining at a temperature between 700 and 1200° C., so as to obtain a mixed oxide phase containing cobalt and/or nickel in the support,
 then carrying out
 b) a step of bringing said support containing said mixed oxide phase into contact with at least one solution containing at least one precursor of cobalt,
 c) a step of bringing said support containing said mixed oxide phase into contact with at least one solution comprising at least one hydrocarbon organic compound of formula $C_xH_y$, it being understood that said hydrocarbon organic compound is in liquid form and that when the solution comprises a solvent, said hydrocarbon organic compound is miscible in the solvent,
 steps b) and c) being able to be performed separately, in any order, or at the same time,
 d) then carrying out a step of drying at a temperature below 200° C.

The applicant has indeed observed that the use of a hydrocarbon organic compound of formula $C_xH_y$ as an organic additive during the preparation of a catalyst containing an active cobalt phase, deposited on a support comprising alumina, silica or silica-alumina, said support also containing a mixed oxide phase containing cobalt and/or nickel made it possible to obtain a catalyst for Fischer-Tropsch synthesis displaying improved catalytic performance.

Indeed, the catalyst according to the invention displays increased activity and increased selectivity relative to catalysts containing a mixed oxide phase containing cobalt and/or nickel in their support but prepared without the addition of at least one hydrocarbon organic compound of formula $C_xH_y$ or relative to additive-containing catalysts with no mixed oxide phase containing cobalt and/or nickel in the support. The use of such an organic compound during the preparation of a cobalt-based catalyst containing a support containing a mixed oxide phase containing cobalt and/or nickel seems to have a synergistic effect on the activity and selectivity in a Fischer-Tropsch process.

Without being bound to any theory, it was discovered that such a catalyst has a dispersion of the cobalt that is substantially greater than that exhibited by catalysts prepared in the absence of such an organic compound. This results in the presence of a greater number of active sites for the catalysts prepared in the presence of at least one hydrocarbon organic compound of formula $C_xH_y$, even if this hydrocarbon organic compound of formula $C_xH_y$ is at least partially eliminated afterwards by a drying and optionally a calcining.

According to one variant, the content of mixed oxide phase in the support is between 0.1 and 50% by weight relative to the weight of the support.

According to one variant, the mixed oxide phase comprises an aluminate of formula $CoAl_2O_4$ or $NiAl_2O_4$ in the case of a support based on alumina or on silica-alumina.

According to one variant, the mixed oxide phase comprises a silicate of formula $Co_2SiO_4$ or $Ni_2SiO_4$ in the case of a support based on silica or on silica-alumina.

According to one variant, the silica content of said support is between 0.5% by weight and 30% by weight relative to the weight of the support before the formation of the mixed oxide phase when the support is a silica-alumina.

Preferably, the hydrocarbon organic compound of formula $C_xH_y$ introduced during step c) is selected from an acyclic or cyclic, saturated or unsaturated hydrocarbon compound with x≥5 and y≥6.

Preferably, the molar ratio of the hydrocarbon organic compound of formula $C_xH_y$ introduced during step c) relative to the cobalt element introduced in step b) is between 0.01 and 5.0 mol/mol.

According to one variant, the content of cobalt element introduced during step b) as active phase is between 1 and 40% by weight expressed as cobalt metal element relative to the total weight of the catalyst.

According to one variant, the catalyst further comprises an element selected from groups VIIIB, IA, IB, IIA, IIB, IIIA, IIIB and VA.

According to one variant, the catalyst further contains an organic compound other than the hydrocarbon organic compound of formula $C_xH_y$, said organic compound containing oxygen and/or nitrogen. According to this variant, the organic compound is selected from a compound comprising one or more chemical functions selected from a carboxylic, alcohol, ether, aldehyde, ketone, amine, nitrile, imide, oxime, urea and amide function.

According to one embodiment, after the drying step d), a calcining step e) is carried out at a temperature of between 200 and 500° C. in an inert atmosphere or in an oxygen-containing atmosphere.

According to one variant, the catalyst obtained in the drying step d) or obtained in the calcining step e) at a temperature of between 200 and 550° C., is reduced.

The invention also relates to the use of the catalyst according to the invention in a Fischer-Tropsch synthesis process wherein the catalyst according to the invention is brought into contact with a feedstock comprising synthesis gas under a total pressure of between 0.1 and 15 MPa, under a temperature of between 150 and 350° C., and at an hourly space velocity of between 100 and 20 000 volumes of synthesis gas per volume of catalyst and per hour with an $H_2/CO$ molar ratio of the synthesis gas of between 0.5 and 4.

Hereinafter, groups of chemical elements are given according to the CAS classification (CRC Handbook of Chemistry and Physics, published by CRC Press, Editor in Chief D. R. Lide, $81^{st}$ edition, 2000-2001). For example, group VIII according to the CAS classification corresponds to the metals of columns 8, 9 and 10 according to the new IUPAC classification.

Textural and structural properties of the support and of the catalyst described below are determined by the characterization methods known to a person skilled in the art. The total pore volume and the pore distribution are determined in the present invention by nitrogen porosimetry as described in the book "Adsorption by powders and porous solids. Principles, methodology and applications", written by F. Rouquérol, J. Rouquérol and K. Sing, Academic Press, 1999.

The specific surface area is understood to mean the BET specific surface area ($S_{BET}$ in $m^2/g$) determined by nitrogen adsorption in accordance with standard ASTM D 3663-78 developed from the Brunauer-Emmett-Teller method described in the journal "The Journal of the American Chemical Society", 1938, 60 (309).

DETAILED DESCRIPTION OF THE INVENTION

The catalyst according to the invention is a catalyst containing an active cobalt phase, deposited on a support comprising alumina, silica or silica-alumina, said support further containing a mixed oxide phase containing cobalt and/or nickel, said catalyst being prepared by a process comprising at least:
   a) a step of bringing a support comprising alumina, silica or silica-alumina into contact with at least one solution containing at least one precursor of cobalt and/or of nickel, then drying and calcining at a temperature between 700 and 1200° C., so as to obtain a mixed oxide phase containing cobalt and/or nickel in the support,
   then carrying out
   b) a step of bringing said support containing said mixed oxide phase into contact with at least one solution containing at least one precursor of cobalt,
   c) a step of bringing said support containing said mixed oxide phase into contact with a solution comprising at least one hydrocarbon organic compound of formula $C_xH_y$, it being understood that said hydrocarbon organic compound is in liquid form and that when the solution comprises a solvent, said hydrocarbon organic compound is miscible in the solvent,
   steps b) and c) being able to be performed separately, in any order, or at the same time,
   d) then carrying out a step of drying at a temperature below 200° C.

The various steps of the process leading to the catalyst according to the invention will be described in detail hereinafter:

Step a) Formation of the Mixed Oxide Phase Containing Cobalt and/or Nickel

The objective of step a) is the formation of a mixed oxide phase containing cobalt and/or nickel in a support comprising alumina, silica or silica-alumina by bringing it into contact with a solution containing at least one precursor of cobalt and/or of nickel, followed by a drying and a high-temperature calcining.

It is known that the presence of a mixed oxide phase containing cobalt and/or nickel in an alumina, silica or silica-alumina support makes it possible to improve the resistance to the phenomenon of chemical and mechanical attrition in a Fischer-Tropsch process, and therefore to stabilize the support.

The formation of the mixed oxide phase in the support, often referred to as the support stabilization step, may be carried out by any method known to a person skilled in the art. It is generally carried out by introducing cobalt and/or nickel in the form of a salt precursor, for example of nitrate type, over the initial support containing alumina, silica or silica-alumina. By calcining at very high temperature, the mixed oxide phase containing cobalt and/or nickel is formed and stabilizes the whole of the support. The cobalt and/or nickel contained in the mixed oxide phase cannot be reduced during the final activation of the Fischer-Tropsch (reduction) catalyst. The cobalt and/or nickel contained in the mixed oxide phase does not therefore constitute the active phase of the catalyst.

According to step (a), a step is carried out of bringing a support comprising alumina, silica or silica-alumina into contact with at least one solution containing at least one precursor of cobalt and/or of nickel, then drying and calcining at a temperature between 700 and 1200° C., so as to obtain a mixed oxide phase containing cobalt and/or nickel in the support.

More particularly, the contacting step a) may be carried out by impregnation, preferably dry impregnation, of a support comprising alumina, silica or silica-alumina, preformed or in powder form, with at least one aqueous solution containing the precursor of cobalt and/or of nickel, followed by a drying and a calcining at a temperature between 700 and 1200° C.

The cobalt is brought into contact with the support by means of any cobalt precursor that is soluble in the aqueous phase. Preferably, the cobalt precursor is introduced in aqueous solution, for example in nitrate, carbonate, acetate or chloride form, in the form of complexes formed with acetylacetonates or of any other inorganic derivative soluble in aqueous solution, which is brought into contact with said support. The cobalt precursor advantageously used is cobalt nitrate or cobalt acetate.

The nickel is brought into contact with the support by means of any nickel precursor that is soluble in the aqueous phase. Preferably, said nickel precursor is introduced in aqueous solution, for example in nitrate, carbonate, acetate, chloride, hydroxide, hydroxycarbonate or oxalate form, in the form of complexes formed with acetylacetonates or of any other inorganic derivative soluble in aqueous solution, which is brought into contact with said support. The nickel precursor advantageously used is nickel nitrate, nickel chloride, nickel acetate or nickel hydroxycarbonate.

The total content of cobalt and/or of nickel is advantageously between 1 and 20% by weight and preferably between 2 and 10% by weight relative to the total mass of the final support.

The drying is advantageously carried out at a temperature between 60° C. and 200° C., preferably for a period ranging from 30 minutes to three hours.

The calcining is carried out at a temperature between 700 and 1200° C., preferably between 850 and 1200° C., and preferably between 850 and 900° C., generally for a period of between one hour and 24 hours and preferably between 2 hours and 5 hours. The calcining is generally carried out under an oxidizing atmosphere, for example in air, or in oxygen-depleted air; it may also be carried out at least partly under nitrogen. It makes it possible to convert the precursors of cobalt and/or of nickel and the alumina and/or silica into the mixed oxide phase containing cobalt and/or nickel.

According to one variant, the calcining may also be carried out in two steps, said calcining is advantageously carried out at a temperature between 300° C. and 600° C. in air for a period of between half an hour and three hours, and then at a temperature between 700° C. and 1200° C., preferably between 850 and 1200° C. and preferably between 850 and 900° C., generally for a period of between one hour and 24 hours, and preferably of between 2 hours and 5 hours.

The support also comprises alumina, silica or silica-alumina.

When the support comprises alumina, it contains more than 50% by weight of alumina relative to the weight of the support before the formation of the mixed oxide phase and, preferably, it contains only alumina. The alumina may be present in a crystallographic form of gamma-, delta-, theta- or alpha-alumina type, taken alone or as a mixture.

In another preferred case, the support comprises silica. In this case, it contains more than 50% by weight of silica relative to the weight of the support before the formation of the mixed oxide phase and, preferably, it contains only silica. Sources of silicon are well known to a person skilled in the art.

In another preferred case, the support comprises a silica-alumina. A support comprising a silica-alumina is understood to mean a support in which the silicon and the aluminum are in the form of agglomerates of silica or alumina respectively, amorphous aluminosilicate or any other mixed phase containing silicon and aluminum, it being understood that the support is not mesostructured. Preferably, the alumina and the silica are present in the form of a mixture of oxides $SiO_2$—$Al_2O_3$. The silica content in the silica-alumina support varies from 0.5% by weight to 30% by weight, preferably from 1% by weight to 25% by weight, and more preferably still from 1.5 to 20% by weight relative to the weight of the support before the formation of the mixed oxide phase.

According to one preferred variant, the support, aside from the mixed oxide phase, consists of alumina, silica or silica-alumina, and particularly preferably the support consists of silica-alumina.

The support also contains a mixed oxide phase containing cobalt and/or nickel. A mixed oxide phase containing cobalt and/or nickel is understood to mean a phase in which cations of cobalt and/or of nickel are combined with the $O^{2-}$-oxide ions of the alumina and/or silica support thus forming a mixed phase containing aluminates and/or silicates containing cobalt and/or nickel. The mixed oxide phase may be in amorphous form or in crystalline form.

When the support is based on alumina, the mixed oxide phase may comprise an aluminate of formula $CoAl_2O_4$ or $NiAl_2O_4$, in amorphous or crystalline form, for example in spinel form.

When the support is based on silica, the mixed oxide phase may comprise a silicate of formula $Co_2SiO_4$ or $Ni_2SiO_4$ (cobalt- or nickelorthosilicate), in amorphous or crystalline form.

When the support is based on silica-alumina, the mixed oxide phase may comprise an aluminate of formula $CoAl_2O_4$ or $NiAl_2O_4$ in amorphous or crystalline form, for example in spinel form, and/or a silicate of formula $Co_2SiO_4$ or $Ni_2SiO_4$, in amorphous or crystalline form.

Generally, the content of the mixed oxide phase in the support is between 0.1 and 50% by weight relative to the support, preferably between 0.5 and 30% by weight, and more preferably between 1 and 20% by weight.

The presence of a mixed oxide phase in the catalyst according to the invention is measured by temperature-programmed reduction (or TPR) such as for example described in *Oil & Gas Science and Technology, Rev. IFP,*

Vol. 64 (2009), No. 1, pp. 11-12. According to this technique, the catalyst is heated in a stream of a reducing agent, for example in a stream of dihydrogen. The measurement of the dihydrogen consumed as a function of the temperature gives quantitative information regarding the reducibility of the species present. The presence of a mixed oxide phase in the catalyst is thus expressed by a consumption of dihydrogen at a temperature above around 800° C.

The support may have a morphology in the form of beads, extrudates (for example of trilobe or quadrilobe shape) or pellets, especially when said catalyst is used in a reactor operating as a fixed bed, or may have a morphology in the form of a powder of variable particle size, especially when said catalyst is used in a bubble-column (or "slurry bubble-column") reactor. The size of the grains of the catalyst may be between a few microns and a few hundred microns. For a "slurry" reactor implementation, the size of the particles of the catalyst is preferentially between 10 microns and 500 microns, preferably between 10 microns and 300 microns, very preferably between 20 and 200 microns, and even more preferably between 30 and 160 microns.

The specific surface area of the support containing the mixed oxide phase is generally between 50 $m^2/g$ and 500 $m^2/g$, preferably between 100 $m^2/g$ and 300 $m^2/g$, more preferably between 150 $m^2/g$ and 250 $m^2/g$. The pore volume of said support is generally between 0.3 ml/g and 1.2 ml/g, and preferably between 0.4 ml/g and 1 ml/g.

Thus, at the end of said step a), said support comprising alumina, silica or silica-alumina further comprises a mixed oxide phase containing cobalt and/or nickel.

Steps b) and c): Introduction of the Active Phase and of the Hydrocarbon Organic Compound of Formula $C_xH_y$ After the formation of the mixed oxide phase, the following steps are carried out in the preparation of the catalyst according to the invention:
- b) a step of bringing said support containing said mixed oxide phase into contact with at least one solution containing at least one precursor of cobalt,
- c) a step of bringing said support containing said mixed oxide phase into contact with a solution comprising at least one hydrocarbon organic compound of formula $C_xH_y$, it being understood that said hydrocarbon organic compound is in liquid form and that when the solution comprises a solvent, said hydrocarbon organic compound is miscible in the solvent.

According to the invention, steps b) and c) may be carried out separately, in any order, or at the same time.

According to a first embodiment, the term "co-impregnation" of the hydrocarbon organic compound denotes that step b) is carried out at the same time as step c).

According to a second embodiment, the term "post-impregnation" of the hydrocarbon organic compound denotes that step b) is carried out before step c).

According to a third embodiment, the term "pre-impregnation" of the hydrocarbon organic compound denotes that step c) is carried out before step b).

Step b) of bringing said support into contact with at least one solution containing at least one cobalt precursor may be carried out by any method well known to a person skilled in the art. Said step b) is preferentially carried out by impregnation of the support by at least one solution containing at least one cobalt precursor. In particular, said step b) can be achieved by dry impregnation, by excess impregnation, or else by deposition—precipitation (as described in U.S. Pat. Nos. 5,874,381 and 6,534,436) according to methods well known to a person skilled in the art. Preferably, said step b) is carried out by dry impregnation, which consists in bringing the catalyst support into contact with a solution containing at least one cobalt precursor, the volume of which is equal to the pore volume of the support to be impregnated. This solution contains the cobalt precursor at the desired concentration.

The cobalt is brought into contact with said support by means of a solution in which the whole cobalt precursor is soluble.

The choice of the solvent in which the cobalt precursor is dissolved depends on the way in which step b) is carried out relative to step c).

If step b) is performed before or after step c), it is possible to use an aqueous solution or an organic solution in which the cobalt precursor is soluble. When introduced in organic solution, said cobalt precursor is for example cobalt acetate or cobalt nitrate. Preferably, said cobalt precursor is introduced in aqueous solution, for example in nitrate, carbonate, acetate or chloride form, in the form of complexes formed with acetylacetonates or of any other inorganic derivative soluble in aqueous solution, which is brought into contact with said support. Use is advantageously made, as cobalt precursor, of cobalt nitrate or cobalt acetate. The content of cobalt element introduced is generally between 1 and 40% by weight, preferably between 2 and 30% by weight, and more preferably between 5 and 25% by weight expressed as cobalt metal element relative to the total weight of the dried catalyst.

The catalyst may advantageously further comprise at least one element selected from an element from groups VIIIB, IA, IB, IIA, IIB, IIIA, IIIB and/or VA.

The preferred possible elements from group VIIIB are platinum, ruthenium and rhodium. The preferred elements from group IA are sodium and potassium. The preferred elements from group IB are silver and gold. The preferred elements from group IIA are manganese and calcium. The preferred element from group IIB is zinc. The preferred elements from group IIIA are boron and indium. The preferred elements from group IIIB are lanthanum and cerium. The preferred element from group VA is phosphorus.

The content of possible element from groups VIIIB, IA, IB, IIA, IIB, IIIA, IIIB and/or VA is between 50 ppm and 20% by weight, preferably between 100 ppm and 15% by weight, and more preferably between 100 ppm and 10% by weight expressed as element relative to the total weight of the catalyst.

According to one variant, when the catalyst contains one or several additional elements from groups VIIIB, IA, IB, IIA, IIB, IIIA, IIIB and/or VA, this or these elements may be either initially present on the support before the preparation of the catalyst, or introduced at any moment of the preparation and by any method known to a person skilled in the art.

Bringing the hydrocarbon organic compound used for the implementation of said step c) into contact with said support is achieved by impregnation, in particular by dry impregnation or excess impregnation, preferentially by dry impregnation. According to one embodiment, said hydrocarbon organic compound, which is in liquid form, is impregnated on said support after solubilization in a solution containing a solvent with which it is miscible enabling a single-phase mixture to be obtained. Preferably, the solvent may be ethanol, isopropanol, ethyl acetate, methyl acetate, tetrahydrofuran. Very preferably, the solvent is ethanol. According to another embodiment, step c) does not involve a solvent in which the organic compound is solubilized, the impregnation solution consists of the hydrocarbon organic compound in the liquid phase.

Said organic compound is a hydrocarbon compound of formula $C_xH_y$. It may be selected from an acyclic or cyclic, saturated or unsaturated hydrocarbon compound with $x \geq 5$ and $y \geq 6$.

In the case of a saturated hydrocarbon compound, it may be linear, branched or cyclic. According to this variant, the hydrocarbon organic compound of formula $C_xH_y$ is selected from linear or branched alkanes or alicyclic compounds, preferably n-heptane, n-octane, n-nonane, n-decane, i-heptane, i-octane, i-nonane, i-decane, cyclopentane, cyclohexane.

In the case of an unsaturated hydrocarbon compound, it may be linear, branched or cyclic. According to this variant, the hydrocarbon organic compound of formula $C_xH_y$ is selected from linear or branched alkenes or alkynes or unsaturated cyclic compounds or aromatic compounds, preferably heptene, octene, nonene, decene, cyclopentadiene, cyclohexene, toluene, cumene, styrene, xylene or ethylbenzene.

The molar ratio of hydrocarbon organic compound of formula $C_xH_y$ introduced during step c) relative to the cobalt element introduced in step b) is between 0.01 and 5.0 mol/mol, preferably between 0.05 and 1.0.

The catalyst according to the invention may comprise, in addition to the hydrocarbon organic compound of formula $C_xH_y$, another organic compound or a group of organic compounds known for their role as additives. The function of the additives is to increase the catalytic activity relative to catalysts without additives. In particular, the catalyst according to the invention may further comprise one or more oxygen-containing and/or nitrogen-containing organic compounds.

Generally, the organic compound is selected from a compound comprising one or more chemical functions selected from a carboxylic, alcohol, ether, aldehyde, ketone, amine, nitrile, imide, oxime, urea and amide function.

The oxygen-containing organic compound may be one or more selected from compounds comprising one or more chemical functions selected from a carboxylic, alcohol, ether, aldehyde or ketone function. By way of example, the oxygen-containing organic compound may be one or more selected from the group consisting of ethanol, ethylene glycol, diethylene glycol, triethylene glycol, a polyethylene glycol (with a molecular weight between 200 and 1500 g/mol), propylene glycol, 2-butoxyethanol, 2-(2-butoxyethoxy)ethanol, 2-(2-methoxyethoxy)ethanol, triethylene glycol dimethyl ether, glycerol, acetophenone, 2,4-pentanedione, pentanone, acetic acid, maleic acid, malonic acid, malic acid, oxalic acid, gluconic acid, tartaric acid, citric acid, succinic acid, γ-ketovaleric acid, γ-valerolactone, 4-hydroxyvaleric acid, 2-pentenoic acid, 3-pentenoic acid, 4-pentenoic acid, a C1-C4 dialkyl succinate, methyl acetoacetate, dibenzofuran, a crown ether, orthophthalic acid and glucose.

The nitrogen-containing organic compound may be one or more selected from compounds comprising one or more chemical functions selected from an amine or nitrile function. By way of example, the nitrogen-containing organic compound may be one or more selected from the group consisting of ethylenediamine, diethylenetriamine, hexamethylenediamine, triethylenetetramine, tetraethylenepentamine, pentaethylenehexamine, acetonitrile, octylamine, guanidine or a carbazole.

The organic compound containing oxygen and nitrogen may be one or more selected from compounds comprising one or more chemical functions selected from a carboxylic, alcohol, ether, aldehyde, ketone, amine, nitrile, imide, amide, urea or oxime function. By way of example, the organic compound containing oxygen and nitrogen may be one or more selected from the group consisting of 1,2-cyclohexanediaminetetraacetic acid, monoethanolamine (MEA), N-methylpyrrolidone, dimethylformamide, ethylenediaminetetraacetic acid (EDTA), alanine, glycine, proline, lysine, nitrilotriacetic acid (NTA), N-(2-hydroxyethyl)ethylenediamine-N,N',N'-triacetic acid (HEDTA), diethylenetriaminepentaacetic acid (DPTA), tetramethylurea, glutamic acid, dimethylglyoxime, bicine or tricine, or else a lactam.

The total molar ratio of oxygen-containing and/or nitrogen-containing organic compound(s) other than the hydrocarbon organic compound of formula $C_xH_y$ relative to the cobalt element introduced in step b) is between 0.01 and 2 mol/mol, preferably between 0.1 and 2 mol/mol, preferably between 0.2 and 1.5 mol/mol, calculated on the basis of the components introduced into the impregnating solution(s).

When the catalyst contains an organic compound other than the hydrocarbon organic compound of formula $C_xH_y$, this organic compound may be either initially present on the support before the preparation of the catalyst, or incorporated into the catalyst at any moment of the preparation and by any method known to a person skilled in the art.

The process for preparing the catalyst according to the invention, in particular steps b) and c), comprises several modes of implementation. They are distinguished in particular by the moment when the organic compound is introduced, which may be carried out either at the same time as the impregnation of the cobalt of the active phase (co-impregnation) or after the impregnation of the cobalt of the active phase (post-impregnation), or before the impregnation of the cobalt of the active phase (pre-impregnation). In addition, it is possible to combine the modes of implementation.

A first mode of implementation consists in carrying out said steps b) and c) simultaneously so that said organic compound and at least said cobalt precursor present in the active phase are co-impregnated on said support (co-impregnation). This first mode of implementation advantageously comprises the implementation of one or more steps b). In particular, one or more steps b) advantageously precede(s) and/or follow(s) said co-impregnation step. This first mode of implementation may also comprise several co-impregnation steps. It should be noted that in the mode of implementation by co-impregnation, a solvent will be selected in which the cobalt precursor and the hydrocarbon organic compound are soluble so as to obtain a single-phase solution. Alternatively, it is possible to use, as co-impregnation solution, a solvent which consists of the hydrocarbon organic compound and in which the cobalt precursor is solubilized.

A second mode of implementation consists in carrying out said step b) prior to said step c) (post-impregnation). In accordance with said second mode of implementation, one or more steps b) of bringing into contact at least the cobalt present in the active phase of the catalyst precede(s) said step c).

A third mode of implementation consists in carrying out said step c) prior to said step b) (pre-impregnation). Advantageously, said step c) is followed by several steps b).

As specified above when step b) is carried out independently of step c), the process for preparing the catalyst is more flexible in terms of choice of solvent for solubilization of the cobalt precursor and of the hydrocarbon organic compound.

When steps b) and c) are carried out separately (post-impregnation or pre-impregnation), a drying step is advantageously carried out between the impregnation steps. The intermediate drying step is carried out at a temperature below 200° C., advantageously between 50 and 180° C., preferably between 70 and 150° C., very preferably between 75 and 130° C. and optionally a maturation period was observed between the impregnation step and the intermediate drying step.

Each of the three modes of implementation described above may be carried out independently so that the catalyst according to the invention is prepared either according to said first mode of implementation, or according to said second mode of implementation or else according to said third mode of implementation. However, it may be advantageous to combine said first mode with said second mode or with said third mode: both the cobalt present in the active phase and the organic compound are deposited at least twice on the catalyst support, namely at least once by co-impregnation and at least once by successive impregnation.

Advantageously, after each impregnation step, whether this is a cobalt or organic compound impregnation step, the impregnated support is left to mature. Maturing allows the impregnation solution to be dispersed homogeneously within the support.

Any maturing step described in the present invention is advantageously carried out at atmospheric pressure, in a water-saturated atmosphere and at a temperature between 17° C. and 50° C., and preferably at room temperature. Generally, a maturing time of between ten minutes and forty-eight hours, and preferably of between thirty minutes and five hours, is sufficient. Longer periods of time are not ruled out but do not necessarily contribute an improvement.

Any impregnation solution described in the present invention may comprise any solvent known to a person skilled in the art that enables a solubilization of the cobalt precursor and/or of the hydrocarbon organic compound in liquid form.

When step b) of impregnating the cobalt is carried out independently of the impregnation of the hydrocarbon organic compound, the solvent used for said step b) is advantageously selected from the group formed by methanol, ethanol, water, phenol, cyclohexanol, isopropanol, ethyl acetate, methyl acetate, tetrahydrofuran, taken alone or as a mixture. The solvent may also be advantageously selected from the group formed by propylene carbonate, DMSO (dimethyl sulfoxide), N-methylpyrrolidone (NMP) or sulfolane, taken alone or as a mixture. A list of common solvents and also their dielectric constant can be found in the book "Solvents and Solvent Effects in Organic Chemistry" C. Reichardt, Wiley-VCH, 3rd edition, 2003, pages 472-474. Very preferably, the solvent used is water or ethanol, alone or as a mixture. When steps b) and c) are carried out at the same time (according to the mode of co-impregnation of the hydrocarbon organic compound with the cobalt), it will be ensured that a solvent in which the cobalt precursor and the hydrocarbon organic compound in liquid form are soluble is used so as to provide a single-phase impregnation solution. For example, it is possible to use a solvent selected from ethanol, isopropanol, acetic acid, methanol or ethylene glycol. It is also possible to use, as co-impregnation solution, a solvent which consists of the hydrocarbon organic compound and in which the cobalt precursor is solubilized.

When step c) is carried out independently of step b), the impregnation solution containing the hydrocarbon organic compound in liquid form may consist of said organic compound, or comprise a solvent in which the hydrocarbon organic compound is solubilized.

When several impregnation steps are carried out, each impregnation step is preferably followed by an intermediate drying step at a temperature below 200° C., advantageously between 50 and 180° C., preferably between 70 and 150° C., very preferably between 75 and 130° C. and optionally a maturation period was observed between the impregnation step and the intermediate drying step.

Drying Step d)

In accordance with the drying step d) of the implementation for the preparation of the catalyst, prepared according to at least one mode of implementation described above, the drying is carried out at a temperature below 200° C., advantageously between 50 and 180° C., preferably between 70 and 150° C., very preferably between 75 and 130° C. The drying step is preferentially carried out for a period of between 1 and 4 hours, preferably in an inert atmosphere or in an oxygen-containing atmosphere.

The drying step can be carried out by any technique known to a person skilled in the art. It is advantageously carried out at atmospheric pressure or at reduced pressure. Preferably, this step is carried out at atmospheric pressure. It is advantageously carried out in a crossed bed using hot air or any other gas. Preferably, when the drying is carried out in a fixed bed, the gas used is either air, or an inert gas such as argon or nitrogen. Very preferably, the drying is carried out in a crossed bed in the presence of nitrogen and/or air. Preferably, the drying step has a short duration of between 5 minutes and 4 hours, preferably of between 30 minutes and 4 hours and very preferably of between 1 hour and 3 hours.

According to a first variant, the drying is conducted so as to keep preferably at least 30% of the hydrocarbon organic compound of formula $C_xH_y$ introduced during an impregnation step, preferably this amount is greater than 50% and even more preferably greater than 70%, calculated on the basis of the carbon remaining on the catalyst. When an organic compound containing oxygen and/or nitrogen other than the hydrocarbon organic compound of formula $C_xH_y$ is present, the drying step is carried out so as to keep preferably at least 30%, preferably at least 50%, and very preferably at least 70% of the amount introduced, calculated on the basis of carbon remaining on the catalyst.

At the end of the drying step d), a dried catalyst is then obtained, which will be subjected to an activation step for the subsequent use thereof in Fischer-Tropsch synthesis.

According to another variant, at the end of the drying step d), a calcining step e) is carried out at a temperature of between 200° C. and 550° C., preferably of between 250° C. and 500° C., in an inert atmosphere (nitrogen for example) or in an oxygen-containing atmosphere (air for example). The duration of this heat treatment is generally between 0.5 hours and 16 hours, preferably between 1 hour and 5 hours. After this treatment, the cobalt of the active phase is thus in oxide form and the catalyst contains no more or very little organic compound introduced during synthesis thereof. However the introduction of the organic compound during the preparation thereof has made it possible to increase the dispersion of the active phase thus leading to a more active and/or more selective catalyst.

Activation (Reduction)

Prior to its use in the catalytic reactor and the implementation of the Fischer-Tropsch process according to the invention, the dried catalyst obtained in step d) or the calcined catalyst obtained in step e) advantageously undergoes a reductive treatment, for example with pure or dilute hydrogen, at high temperature. This treatment makes it possible to activate said catalyst and to form particles of cobalt metal in the zero-valent state. The temperature of this reductive treatment is preferentially between 200 and 500° C. and the duration thereof is between 2 and 20 hours.

This reductive treatment is carried out either in situ (in the same reactor as the one where the Fischer-Tropsch reaction is carried out according to the process of the invention), or ex situ before being loaded into the reactor.

Fischer-Tropsch Process

A final subject of the invention is the use of the catalyst according to the invention in a Fischer-Tropsch synthesis process.

The Fischer-Tropsch process according to the invention leads to the production of essentially linear and saturated $C5_+$ hydrocarbons (having at least 5 carbon atoms per molecule). The hydrocarbons produced by the process of the invention are thus essentially paraffinic hydrocarbons, the fraction of which having the highest boiling points can be converted with a high yield to middle distillates (diesel and kerosene cuts) by a hydroconversion process such as catalytic hydrocracking and/or hydroisomerization.

The feedstock used for the implementation of the process of the invention comprises synthesis gas. Synthesis gas is a mixture comprising in particular carbon monoxide and hydrogen having $H_2/CO$ molar ratios that may vary in a ratio of 0.5 to 4 depending on the process by which it was obtained. The $H_2/CO$ molar ratio of the synthesis gas is generally close to 3 when the synthesis gas is obtained from the hydrocarbon or alcohol steam reforming process. The $H_2/CO$ molar ratio of the synthesis gas is of the order of 1.5 to 2 when the synthesis gas is obtained from a partial oxidation process. The $H_2/CO$ molar ratio of the synthesis gas is generally close to 2.5 when it is obtained from a thermal reforming process. The $H_2/CO$ molar ratio of the synthesis gas is generally close to 1 when it is obtained from a process for gasification and reforming of $CO_2$.

The catalyst used in the hydrocarbon synthesis process according to the invention may be implemented in various types of reactors, for example fixed-bed, moving-bed, ebullated-bed or else three-phase fluidized-bed reactors. The implementation of the catalyst suspended in a three-phase fluidized reactor, preferentially of bubble column type, is preferred. In this preferred implementation of the catalyst, said catalyst is divided in the form of a very fine powder, particularly of the order of a few tens of microns, this powder forming a suspension with the reaction medium. This technology is also known under the "slurry" process terminology by a person skilled in the art.

The hydrocarbon synthesis process according to the invention is performed under a total pressure of between 0.1 and 15 MPa, preferably between 0.5 and 10 MPa, under a temperature of between 150 and 350° C., preferably between 180 and 270° C. The hourly space velocity is advantageously between 100 and 20 000 volumes of synthesis gas per volume of catalyst and per hour (100 to 20 000 $h^{-1}$) and preferably between 400 and 10 000 volumes of synthesis gas per volume of catalyst and per hour (400 to 10 000 $h^{-1}$).

The following examples demonstrate the gains in performance regarding the catalysts according to the invention.

EXAMPLES

Example 1 (Comparative): Catalyst A of Formula $Co/Al_2O_3$

A catalyst A comprising cobalt deposited on an alumina support is prepared by dry impregnation of an aqueous solution of cobalt nitrate so as to deposit, in two successive steps, around 10% by weight of Co on a gamma-alumina powder (PURALOX® SCCa 5/170, SASOL) having a mean particle size equal to 80 μm, a surface area of 165 $m^2/g$ and a pore volume measured by nitrogen adsorption isotherm of 0.4 ml/g.

After a first dry impregnation, the solid is dried in a crossed bed at 120° C. for 3 h in air and then calcined at 400° C. for 4 h in a crossed bed under a stream of air. The intermediate catalyst contains around 6% by weight of Co. It is subjected to a second step of dry impregnation using a solution of cobalt nitrate. The solid obtained is dried in a crossed bed at 120° C. for 3 h in air and then calcined at 400° C. for 4 h in a crossed bed under a stream of air. The final catalyst A is obtained which contains 10.5% by weight of Co (in $Co_3O_4$ oxide form).

Example 2 (Comparative): Catalyst B of Formula $Co/Al_2O_3$—$SiO_2$

A catalyst B comprising cobalt deposited on a silica-alumina support is prepared by dry impregnation of an aqueous solution of cobalt nitrate so as to deposit, in one step, around 10% by weight of Co on a silica-alumina initially containing 5% by weight of $SiO_2$ and having a specific surface area of 180 $m^2/g$ and a pore volume of 0.8 ml/g.

After the dry impregnation, the solid is dried in a crossed bed at 120° C. for 3 h in air and then calcined at 400° C. for 4 h in a crossed bed. The final catalyst B is obtained which contains 9.9% by weight of Co (in $Co_3O_4$ oxide form).

Example 3 (Comparative): Catalyst C of Formula $Co/CoAl_2O_4$—$Al_2O_3$—$SiO_2$

A catalyst C comprising cobalt deposited on a support, based on a mixed oxide phase (in spinel form) included in a silica-alumina, is prepared by dry impregnation of an aqueous solution of cobalt nitrate so as to deposit, in one step, around 10% by weight of cobalt on the support.

The spinel present in the support of the catalyst C is a simple spinel formed of cobalt aluminate, which is included in a silica-alumina containing 5% by weight of $SiO_2$, and having a specific surface area of 180 $m^2/g$ and a pore volume of 0.8 ml/g. The preparation of the spinel included in the silica-alumina is carried out by dry impregnation of an aqueous solution of cobalt nitrate so as to introduce 5% by weight of Co into said silica-alumina. After drying at 120° C. for 3 hours, the solid is calcined at 850° C. for 4 hours in air. The support for the catalyst denoted by C' is formed of 5% by weight of cobalt in the form of cobalt aluminate (i.e. 15% by weight of spinel) in the silica-alumina.

The cobalt-based active phase is then deposited on said support in one step, by dry impregnation, according to a protocol that is identical to that described for the preparation of catalyst B. The drying and calcining steps are also performed under the same operating conditions as those of example 2. The concentration of cobalt in the solution of cobalt nitrate, used for the successive impregnations, is chosen in order to obtain the catalyst C with the desired final Co content.

The final catalyst C has a total cobalt content of 15.7% by weight (the content of Co present in the spinel phase being included) and a content of cobalt in $Co_3O_4$ oxide form of 10.7% by weight.

Example 4 (Comparative): Catalyst D of Formula $Co/CoAl_2O_4$—$Al_2O_3$—$SiO_2$ Containing Citric Acid (Co-Impregnation)

A catalyst D comprising cobalt and citric acid deposited on a support, based on a spinel included in a silica-alumina, is prepared by dry impregnation of an aqueous solution of cobalt nitrate and of citric acid so as to deposit around 10% by weight of cobalt on the support.

The cobalt-based active phase is deposited on the support C' of example 3 in one step, by dry impregnation of a solution containing cobalt nitrate and citric acid (Sigma Aldrich®, >99%) in a citric acid: Co molar ratio of 0.5. After dry impregnation, the solid undergoes a maturation in a water-saturated atmosphere for 9 hours at room temperature and then is dried in a crossed bed at 120° C. for 3 h in air, and then treated under nitrogen at 400° C. for 4 h in a crossed bed.

The final catalyst D has a total cobalt content of 14.1% by weight (the content of Co present in the spinel phase being included) and a content of cobalt in $Co_3O_4$ oxide form of 9.1% by weight.

Example 5 (Comparative): Catalyst E of Formula Co/CoAl$_2$O$_4$—I$_2$O$_3$—SiO$_2$ Containing Citric Acid (Post-Impregnation)

A catalyst E comprising cobalt and citric acid deposited on a support, based on a spinel included in a silica-alumina, is prepared by dry impregnation of an aqueous solution of cobalt nitrate, and then of an aqueous solution of citric acid so as to deposit around 10% by weight of cobalt on the support.

The cobalt-based active phase is deposited on the support C' of example 3 in one step, by dry impregnation of a solution containing cobalt nitrate. After dry impregnation, the solid undergoes drying in a crossed bed at 120° C. for 3 h in air.

In a second step, the citric acid is deposited on the preceding solid in one step, by dry impregnation of a solution containing citric acid (Sigma Aldrich®, >99%) at a concentration for attaining a citric acid: Co molar ratio of 0.5 on the final catalyst. After dry impregnation, the solid undergoes a maturation in a water-saturated atmosphere for 9 hours at room temperature and then is dried in a crossed bed at 120° C. for 3 h in air, and then treated under nitrogen at 400° C. for 4 h in a crossed bed.

The final catalyst E has a total cobalt content of 14.0% by weight (the content of Co present in the spinel phase being included) and a content of cobalt in $Co_3O_4$ oxide form of 9.0% by weight.

Example 6 (According to the Invention): Catalyst F of Formula Co/CoAl$_2$O$_4$—Al$_2$O$_3$—SiO$_2$ Containing n-Octane A catalyst F comprising cobalt and n-octane deposited on a support, based on a spinel included in a silica-alumina, is prepared by dry impregnation of an ethanolic solution of cobalt nitrate and of n-octane so as to deposit around 10% by weight of cobalt on the support.

The cobalt-based active phase is deposited on the support C' of example 3 in one step, by dry impregnation of an ethanolic solution containing cobalt nitrate and n-octane (Sigma Aldrich®, >98%) in an n-octane: Co molar ratio of 1.0. After dry impregnation, the solid undergoes a maturation in a water-saturated atmosphere for 9 hours at room temperature and then is dried in a crossed bed at 120° C. for 3 h in air, and then treated under nitrogen at 400° C. for 4 h in a crossed bed.

The final catalyst F has a total cobalt content of 14.9% by weight (the content of Co present in the spinel phase being included) and a content of cobalt in $Co_3O_4$ oxide form of 9.9% by weight.

Example 7 (According to the Invention): Catalyst G of Formula Co/CoAl$_2$O$_4$—Al$_2$O$_3$—SiO$_2$ Containing Xylene A catalyst G comprising cobalt and xylene deposited on a support, based on a spinel included in a silica-alumina, is prepared by dry impregnation of an aqueous solution of cobalt nitrate, and then of an ethanolic solution of xylenes so as to deposit around 10% by weight of cobalt on the support.

The cobalt-based active phase is deposited on the support C' of example 3 in one step, by dry impregnation of a solution containing cobalt nitrate. After dry impregnation, the solid undergoes drying in a crossed bed at 120° C. for 3 h in air.

In a second step, the xylene is deposited on the preceding solid in one step, by dry impregnation of an ethanolic solution containing xylene (mixture of the 3 xylene isomers, Sigma Aldrich®, >98.5%) at a concentration for attaining a xylene: Co molar ratio of 0.5 on the final catalyst. After dry impregnation, the solid undergoes a maturation in a water-saturated atmosphere for 9 hours at room temperature and then is dried in a crossed bed at 120° C. for 3 h in air, and then treated under nitrogen at 400° C. for 4 h in a crossed bed.

The final catalyst G has a total cobalt content of 15.1% by weight (the content of Co present in the spinel phase being included) and a content of cobalt in $Co_3O_4$ oxide form of 10.1% by weight.

Example 8 (According to the Invention): Catalyst H of formula: Co/CoAl$_2$O$_4$—Al$_2$O$_3$—SiO$_2$ Containing Ethylcyclohexane A catalyst H comprising cobalt and ethylcyclohexane deposited on a support, based on a spinel included in a silica-alumina, is prepared by dry impregnation of an ethanolic solution of ethylcyclohexane, and then of an aqueous solution of cobalt nitrate so as to deposit around 10% by weight of cobalt on the support.

The ethylcyclohexane is deposited on the support C' of example 3 in one step, by dry impregnation of an ethanolic solution containing ethylcyclohexane (Sigma Aldrich®, >99%) at a concentration for attaining an ethylcyclohexane: Co molar ratio of 1.0 on the final catalyst. After dry impregnation, the solid undergoes a maturation in a water-saturated atmosphere for 9 hours at room temperature and then is dried in a crossed bed at 120° C. for 3 h in air.

In a second step, the cobalt-based active phase is deposited on the preceding solid in one step, by dry impregnation of a solution containing cobalt nitrate. After dry impregnation, the solid undergoes a maturation in a water-saturated atmosphere for 9 hours at room temperature and then is dried in a crossed bed at 120° C. for 3 h in air, and then treated under nitrogen at 400° C. for 4 h in a crossed bed.

The final catalyst H has a total cobalt content of 14.7% by weight (the content of Co present in the spinel phase being included) and a content of cobalt in $Co_3O_4$ oxide form of 9.7% by weight.

Example 9 (According to the Invention): Catalyst I of Formula Co/CoAl$_2$O$_4$—Al$_2$O$_3$—SiO$_2$ Containing Xylene The catalyst I is prepared in a manner similar to the catalyst G except that it does not undergo a heat treatment under nitrogen at 400° C. at the end of the preparation.

Example 10 (According to the Invention): Catalyst J of Formula Co/CoAl$_2$O$_4$—Al$_2$O$_3$—SiO$_2$ Containing Xylene A catalyst J comprising cobalt and xylene deposited on a support, based on a spinel included in a silica-alumina, is prepared by dry impregnation of an aqueous solution of cobalt nitrate, and then of a mixture of xylenes so as to deposit around 10% by weight of cobalt on the support.

The cobalt-based active phase is deposited on the support C' of example 3 in one step, by dry impregnation of an aqueous solution containing cobalt nitrate. After dry impregnation, the solid undergoes drying in a crossed bed at 120° C. for 3 h in air.

In a second step, the xylene is deposited on the preceding solid in one step, by dry impregnation of a mixture of xylenes (mixture of the 3 xylene isomers, Sigma Aldrich®, >98.5%) so as to attain a xylene: Co molar ratio of 2.0 on the final catalyst. After dry impregnation, the solid undergoes a maturation in a water-saturated atmosphere for 9 hours at room temperature and then is dried in a crossed bed at 120° C. for 3 h in air, and then treated under nitrogen at 400° C. for 4 h in a crossed bed.

The final catalyst J has a total cobalt content of 15.3% by weight (the content of Co present in the spinel phase being included) and a content of cobalt in Co$_3$O$_4$ oxide form of 10.3% by weight.

Example 11: Catalytic Performance of Catalysts A to J in Fischer-Tropsch Reaction The catalysts A, B, C, D, E, F, G, H, I and J, before being tested in Fischer-Tropsch synthesis, are reduced in situ under a stream of pure hydrogen at 400° C. for 16 hours. The Fischer-Tropsch synthesis reaction is performed in a fixed-bed tubular reactor operating continuously.

Each of the catalysts is in powder form with a diameter of between 40 and 150 microns.

The test conditions are as follows:
Temperature=216° C.
Total pressure=2 MPa
Hourly space velocity (HSV)=4100 NL/h$^{-1}$/kg$_{catalyst}$
H$_2$/CO molar ratio=2/1

The results, expressed in terms of activity (conversion of CO in %) and selectivity (weight percentage of C$_8^+$ hydrocarbons over all of the products formed), appear in table 1.

TABLE 1

| catalytic performance of each catalyst | | |
| --- | --- | --- |
| Catalyst | Conversion of CO at 70 h under reaction stream (%) | C$_8^+$ selectivity at 70 h under reaction stream (% by weight) |
| A (comparative) | 27.5 | 57.1 |
| B (comparative) | 38.1 | 65.9 |
| C (comparative) | 44.7 | 68.0 |
| D (comparative) | 30.8 | 53.3 |
| E (comparative) | 41.3 | 56.1 |
| F (invention) | 56.0 | 69.8 |
| G (invention) | 52.5 | 70.2 |
| H (invention) | 50.8 | 68.0 |
| I (invention) | 53.5 | 67.2 |
| J (invention) | 53.2 | 70.3 |

The results in table 1 show that the catalysts according to the invention are more active and/or more selective than the catalysts known from the prior art.

This listing of claims will replace all prior versions, and listings, of claims in the application:

The invention claimed is:

1. A catalyst comprising an active phase consisting of cobalt, deposited on a support consisting of silica-alumina and a mixed oxide phase of cobalt, said catalyst being prepared by a process comprising at least:
    a) contacting a support comprising silica-alumina with at least one solution comprising at least one precursor of cobalt, then drying and calcining at a temperature of 700 to 1200° C., so as to obtain a mixed oxide phase comprising cobalt in the support, then
    b) contacting said support containing said mixed oxide phase with at least one solution comprising at least one precursor of cobalt,
    c) contacting said support containing said mixed oxide phase with a solution containing at least one liquid hydrocarbon organic compound of formula C$_x$H$_y$, and when the solution comprises a solvent, said hydrocarbon organic compound is miscible in the solvent,
        b) and c) being performed separately, in any order, or at the same time, then
    d) drying at a temperature below 200° C.

2. The catalyst as claimed in claim 1, wherein the content of mixed oxide phase in the support is between 0.1 and 50% by weight relative to the weight of the support.

3. The catalyst as claimed in claim 1, wherein the mixed oxide phase comprises an aluminate of formula CoAl$_2$O$_4$.

4. The catalyst as claimed in claim 1, wherein the mixed oxide phase comprises a silicate of formula Co$_2$SiO$_4$.

5. The catalyst as claimed in claim 1, wherein the silica content of said support is between 0.5% by weight and 30% by weight relative to the weight of the support before the formation of the mixed oxide phase.

6. The catalyst as claimed in claim 1, wherein the hydrocarbon organic compound of formula CxHy introduced during c) is an acyclic or cyclic, saturated or unsaturated hydrocarbon compound with x≥5 and y≥6.

7. The catalyst as claimed in claim 6, wherein the hydrocarbon organic compound of formula C$_x$H$_y$ is n-heptane, n-octane, n-nonane, n-decane, i-heptane, i-octane, i-nonane, i-decane, cyclopentane, cyclohexane, heptene, octene, nonene, decene, cyclopentadiene, cyclohexene, toluene, cumene, styrene, xylene or ethylbenzene.

8. The catalyst as claimed in claim 1, wherein the molar ratio of hydrocarbon organic compound of formula C$_x$H$_y$ introduced during c) relative to the cobalt element introduced in b) is between 0.01 and 5.0 mol/mol.

9. The catalyst as claimed in claim 1, wherein the content of cobalt element introduced during b) as active phase is between 1 and 40% by weight expressed as cobalt metal element relative to the total weight of the dried catalyst.

10. The catalyst as claimed in claim 1, wherein, after the drying in d), e) calcining is carried out at a temperature of between 200 and 550° C. in an inert atmosphere or in an oxygen-containing atmosphere.

11. The catalyst as claimed in claim 1, wherein the catalyst obtained in the drying in d) or obtained in the calcining in e) at a temperature of between 200 and 500° C., is reduced.

12. A Fischer-Tropsch process for synthesizing hydrocarbons, wherein the catalyst as claimed in claim 1 is brought into contact with a feedstock comprising synthesis gas under a total pressure of between 0.1 and 15 MPa, under a temperature of between 150 and 350° C., and at an hourly space velocity of between 100 and 20 000 volumes of synthesis gas per volume of catalyst and per hour with an $H_2/CO$ molar ratio of the synthesis gas of between 0.5 and 4.

13. A process for the preparation of a catalyst comprising an active phase consisting of cobalt, deposited on a support consisting of silica-alumina and a cobalt a mixed oxide phase, said process comprising at least:
  a) contacting a support comprising alumina, silica or silica-alumina with at least one solution comprising at least one precursor of cobalt, then drying and calcining at a temperature between 700 and 1200° C., so as to obtain a mixed oxide phase containing cobalt in the support, then
  b) contacting said support containing said mixed oxide phase with at least one solution comprising at least one precursor of cobalt,
  c) contacting said support containing said mixed oxide phase with a solution of at least one liquid hydrocarbon organic compound of formula $C_xH_y$, and when the solution comprises a solvent, said hydrocarbon organic compound is miscible in the solvent,
  b) and c) being performed separately, in any order, or at the same time, then
  d) drying at a temperature below 200° C.

* * * * *